US008348448B2

(12) United States Patent
Orozco et al.

(10) Patent No.: US 8,348,448 B2
(45) Date of Patent: Jan. 8, 2013

(54) HEADGEAR FOR MOUNTING SURGICAL HEADLIGHT

(75) Inventors: Walter Antonio Orozco, Jacksonville, FL (US); James D. Hunter, Hilliard, FL (US)

(73) Assignee: Sunoptic Technologies LLC, Jacksonville, FL (US)

( * ) Notice: Subject to any disclaimer, the term of this patent is extended or adjusted under 35 U.S.C. 154(b) by 147 days.

(21) Appl. No.: 13/100,404

(22) Filed: May 4, 2011

(65) Prior Publication Data

US 2012/0281429 A1 Nov. 8, 2012

(51) Int. Cl.
*F21V 21/08* (2006.01)

(52) U.S. Cl. ................ 362/105; 362/551; 2/905; 2/183; 2/171; 2/182.2

(58) Field of Classification Search .................. 362/105, 362/551, 103; 2/171, 182.2, 182.3, 183, 2/905
See application file for complete search history.

(56) References Cited

U.S. PATENT DOCUMENTS

| | | | |
|---|---|---|---|
| 3,745,993 A * | 7/1973 | Feinbloom | 600/249 |
| 3,830,230 A | 8/1974 | Chester | |
| D238,958 S | 2/1976 | Feinbloom | |
| D266,192 S | 9/1982 | Feinbloom et al. | |
| 4,616,257 A * | 10/1986 | Kloots et al. | 348/370 |
| D300,868 S | 4/1989 | Conforti | |
| 5,115,382 A * | 5/1992 | Smith | 362/105 |
| 5,638,551 A | 6/1997 | Lallemand | |
| D383,229 S | 9/1997 | Kiichiro | |
| D441,111 S | 4/2001 | Van Der Bel | |
| 6,226,802 B1 | 5/2001 | Sasaki et al. | |
| D489,838 S | 5/2004 | Opolka | |
| 6,896,389 B1 | 5/2005 | Paul | |
| D560,009 S | 1/2008 | Spartano et al. | |
| 7,314,300 B1 | 1/2008 | Dorr et al. | |
| 2001/0022005 A1 | 9/2001 | Sasaki et al. | |
| 2005/0262619 A1 | 12/2005 | Musal et al. | |
| 2009/0225534 A1 | 9/2009 | Thomas et al. | |
| 2009/0323317 A1 | 12/2009 | Spartano et al. | |
| 2010/0050324 A1 | 3/2010 | Musal | |
| 2010/0095438 A1 | 4/2010 | Moelker | |
| 2010/0277894 A1 | 11/2010 | Kim | |

OTHER PUBLICATIONS

LIT Surgical, "ONE HeadLIT", 4 page brochure, 2008 (month unknown).

* cited by examiner

*Primary Examiner* — Ali Alavi
(74) *Attorney, Agent, or Firm* — Howson & Howson LLP

(57) ABSTRACT

Headgear for mounting a headlight on a surgeon's head includes a headband and a stabilizer. The headband encircles the wearer's head and the stabilizer is connectable to a rear section of the headband for engaging and cradling a substantial portion of at least a lower back region of a wearer's head when the headgear is worn by the wearer. The stabilizer includes a peripheral extending portion extending beneath the headband on opposite sides of the wearer's head corresponding to a location of a lower portion of an occipital bone of the wearer's head and a peripheral portion extending above the headband on opposite sides of the wearer's head corresponding to a location of a top of the occipital bone. The headgear can also include a connection element for removably connecting the stabilizer to the headband so that the headgear can be worn with or without the stabilizer.

19 Claims, 4 Drawing Sheets

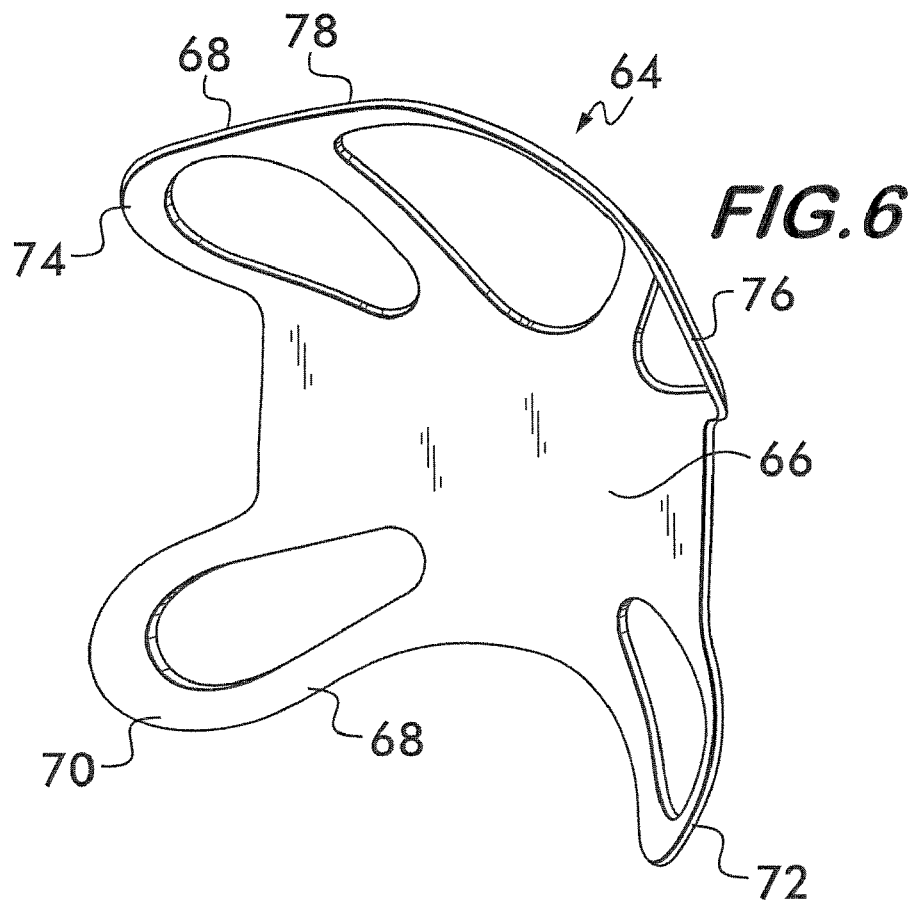
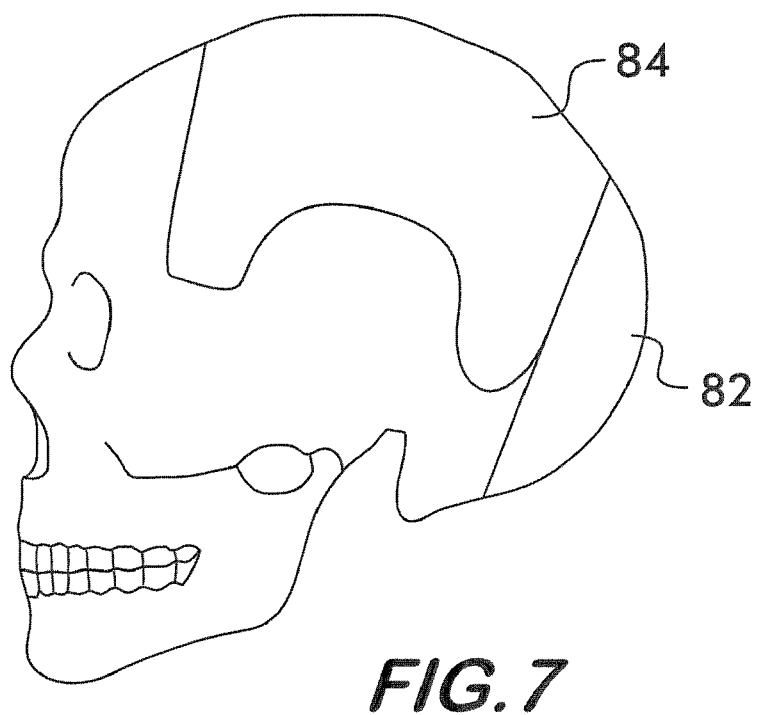

HEADGEAR FOR MOUNTING SURGICAL HEADLIGHT

BACKGROUND OF THE INVENTION

The present invention relates to surgical headlight systems, and more particularly, the present invention relates to headgear for mounting headlights on the head of a surgeon.

Headlights are worn on the head of surgeons, technicians, and like individuals for directing a spotlight beam of intense light coincident with the wearer's line of sight, independent from overhead and/or ambient lighting. Headlight systems typically include a headlamp that receives an emitting end of a fiber optic cable and that focuses and directs the light from the cable into a beam aimed forward of the wearer. The headlamp includes an assembly of optic elements that is preferably configured in a tubular elbow which depends from a headband of headgear at the wearer's forehead to a location approximately between the wearer's eyes.

An example of a headlight system is disclosed by U.S. Pat. No. 7,314,300 B1 issued to Don et al. which is assigned to Sunoptic Technologies LLC, the assignee of the present application. FIG. 1 of U.S. Pat. No. 7,314,300 B1 illustrates an example of a headlamp mounted to headgear worn by a surgeon. The headgear includes a headband encircling the head of its wearer and extending above the wearer's ears and across the wearer's forehead and rear of the wearer's head. The headgear also includes a support or top head strap that extends over the top of the wearer's head and connects to opposite side sections of the headband directly above the ears of the wearer. The headgear supports the headlamp on the headband at a location corresponding to the center of the wearer's forehead. The headgear also guides fiber optic cables extending from the headlamp toward the rear of the wearer's head so that the cables do not interfere with the surgeon's vision or movements.

Additional illustrations of headgear for surgical headlight systems are provided by U.S. Pat. No. 4,616,257 issued to Kloots et al., U.S. Pat. No. 3,830,230 issued to Chester, U.S. Pat. No. 3,745,993 issued to Feinbloom and U.S. Design Pat. Nos. D.238,958 issued to Feinbloom, D.266,192 issued to Feinbloom et al., and D.441,111 S issued to Van Der Bel.

A surgeon may be required to continuously wear the headgear and headlamp for many hours during the course of delicate or complicated surgery. During this time, the surgeon may be required to move within the operating room, for instance, from one side of an operating table to the other, and will frequently change the angle of his/her head relative to the horizontal such as by looking down, looking up, and/or looking to the side at the patient, equipment within the operating room, or the like. Throughout this entire time, it is imperative that the headgear and headlamp remain stationary relative to the head of the wearer in a stable condition. The headgear should not loosen, move relative to the head, or become dislodged. Such events may distract the surgeon and possibly interrupt the surgical procedure. For this reason, it is common practice to tighten conventional headgear as tight as possible to the head of the surgeon to ensure stability. However, such tightening typically leads to discomfort which also may be distracting to the surgeon.

Although the above referenced headgear for mounting surgical headlights may be satisfactory for their intended purposes, there is a need for headgear for a surgical headlight system which can be worn in a manner providing greater stability of the headgear on the head of the surgeon. The headgear should provide this improved stability without the need of over-tightening the headgear and without sacrificing comfort. Thus, surgeons should be able to wear the headgear continuously for many hours in a stable and comfortable manner so as not to provide discomfort or distraction during the course of a surgical procedure.

BRIEF SUMMARY OF THE INVENTION

According to the present development, headgear for mounting a headlight is provided. The headgear has an elongate headband for encircling the head of a wearer. The headband is such that it permits the majority of the wearer's head to be uncovered and exposed to ambient conditions. The headgear also includes a stabilizer connectable to the rear of the headband. The stabilizer engages and cradles a rear of a wearer's head when the headgear is worn by a wearer. The stabilizer has portions that extend lower than a rear section of the headband on opposite sides of the wearer's head and portions that extend above a rear section of the headband on opposite sides of the wearer's head.

According to one contemplated embodiment of the above referenced headgear, the headband is elongate and endless and includes a front section for extending laterally across a forehead of the wearer, a rear section for extending laterally across a rear of the wearer's head, and side sections extending across a side of the wearer's head above ears of the wearer. The headgear further includes an elongate support strap having one end connected to the front section of the headband and an opposite end connected to the rear section of the headband. The headband and support strap have relatively narrow widths thereby permitting a majority of the wearer's head to remain uncovered by the headgear and exposed to ambient conditions. The portion of the stabilizer extending above the headband includes flaps that extend on opposite sides of the support strap. According to at least some embodiments, the stabilizer is removably connected to the headband with hook-and-loop fasteners or the like such that the headgear can be worn without the stabilizer when the stabilizer is removed from the headband and such that the headgear can be worn with the stabilizer when the stabilizer is connected to the headband.

According to another aspect of the development, a fiber optic surgical headlight system is provided. The system includes headgear for being worn on a head of a surgeon and a headlamp mounted on the headgear. The headgear includes an elongate headband for encircling the head of a wearer. The headband includes a front section for extending laterally across a forehead of the wearer and on which the headlamp is mounted. The headband also includes a rear section that extends laterally across a rear of the wearer's head and side sections extending across a side of the wearer's head above the wearer's ears. The headgear also includes an elongate support strap having one end connected to the front section of the headband adjacent and directly above the headlamp and an opposite end connected to the rear section of the headband. The headgear further includes a stabilizer removably connected to the rear of the headband for engaging and cradling a rear of the wearer's head when the headgear is worn by a wearer and when the stabilizer is connected to the headband. When worn, the stabilizer is of a size to extend over a significant portion of the back of the wearer's head such that the stabilizer extends over the back of the wearer's head corresponding to a majority of an occipital bone of the wearer including from a lower portion of the occipital bone to an upper portion of the occipital bone and onto a parietal bone of the wearer.

BRIEF DESCRIPTION OF THE DRAWINGS

The features and advantages of the present invention should become apparent from the following description when taken in conjunction with the accompanying drawings, in which:

FIG. 6 is a perspective view of the stabilizer removed from the headgear of FIG. 1; and FIG. 7 is a side elevation of a human skull showing the general location of the occipital cranial bone and parietal cranial bone.

DETAILED DESCRIPTION OF THE INVENTION

Figure 1:
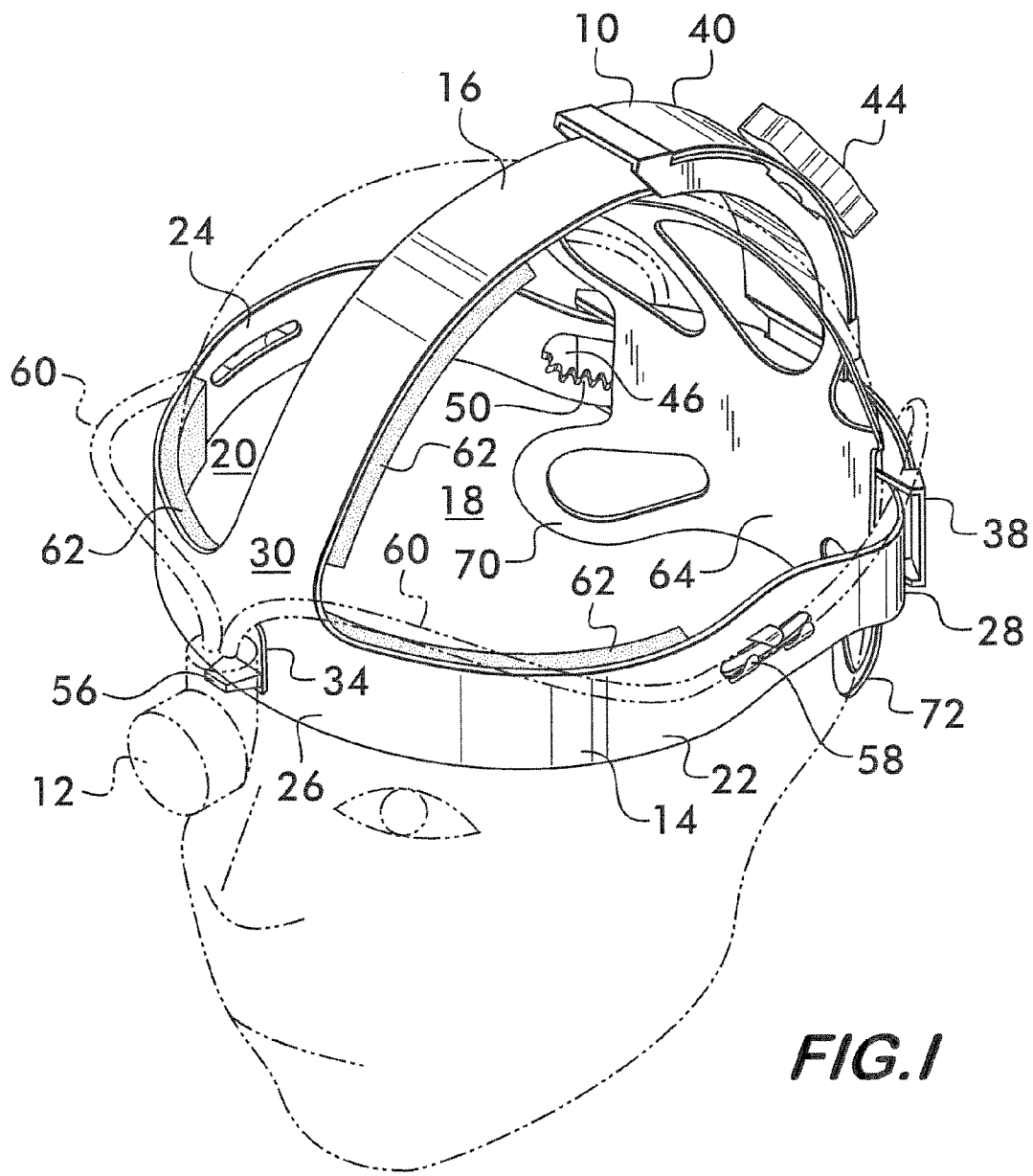
FIG. 1 is a perspective view of headgear according to the present invention.

The headgear 10 of the present invention provides a means for mounting a headlamp 12 or the like in a desired position on the head of a surgeon or other wearer. Typically, the headlamp 12 will be mounted to the headgear 10 such that it extends downwardly and forwardly from a location corresponding generally to the front and center of the forehead of a surgeon or other wearer of the headgear 10. The headgear 10 of the present invention has means for providing improved stability when the headgear 10 is worn while also maximizing comfort. Accordingly, there is no need to tighten or overtighten the headgear 10 of the present invention on the head to an extent that causes discomfort to the wearer.

The headgear 10 has a generally openwork construction such that it is lightweight and does not trap or inhibit the transfer of heat from the wearer's head or inhibit the majority of the head to be exposed to ambient conditions. Thus, when the headgear 10 is worn, the majority of the wearer's head located above the wearer's ears is uncovered by the headgear and is exposed to ambient conditions. For this purpose, the headgear 10 includes a relatively thin and elongate headband component 14 and a relative thin and elongate top head support strap component 16 with large openings, 18 and 20, being provided between the support strap 16 and opposite sides of the headband 14. See FIG. 1.

Figure 2:
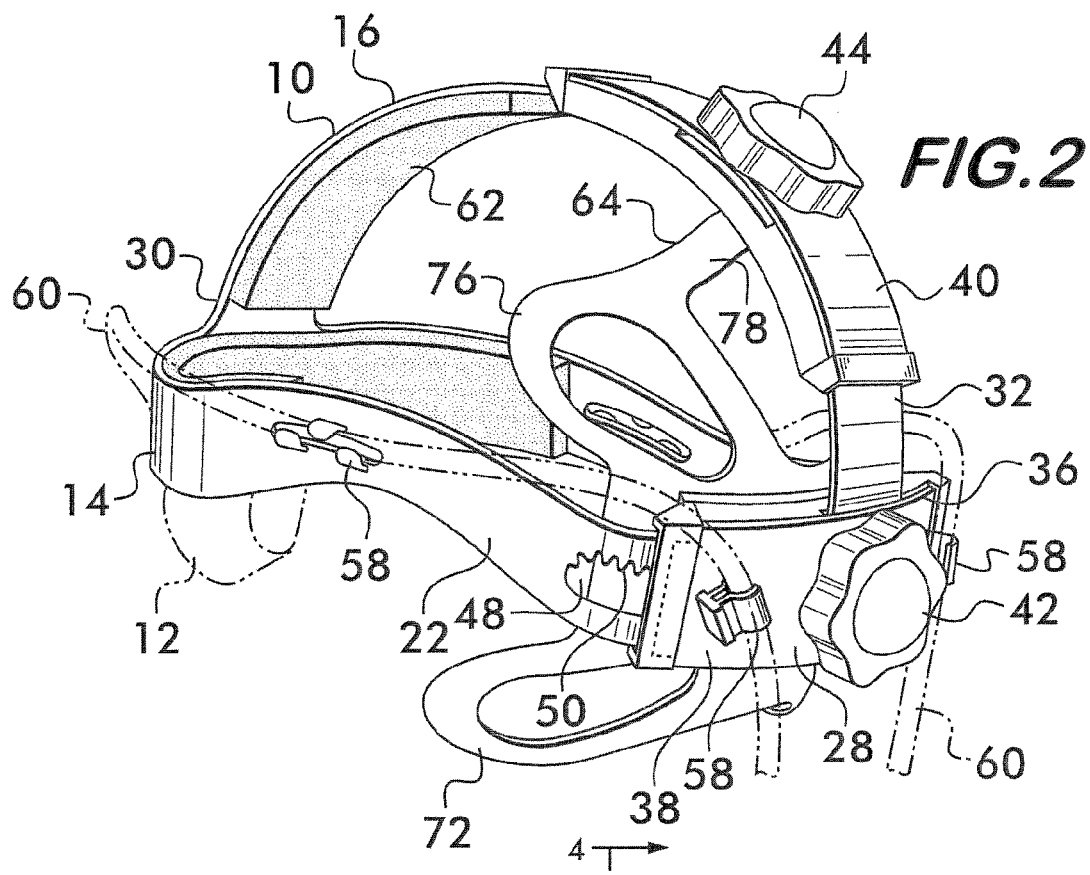
FIG. 2 is a further perspective view of the headgear of FIG. 1.

When assembled, the headband 14 is endless and generally ring-shaped and is formed by an elongate band of material having a relatively narrow width "W1". When worn, the headband 14 engages and encircles the head of the wearer extending laterally across the forehead and rear of the wearer's head and laterally across each side of the head above the ears of the wearer. As best illustrated in FIG. 2, each side section, 22 and 24, of the headband 14 has a generally upward curved portion where the headband 14 extends above and accommodates the ears of the wearer. This permits the front and rear sections, 26 and 28, of the headband 14 to extend at lower positions across the forehead and rear of the head of the wearer.

The top head support strap 16 of the headgear 10 is also relatively elongate and of a relatively narrow width "W2". A front end 30 of the support strap 14 connects and extends from the front section 26 of the headband 14 adjacent and directly above the headlamp 12, and a rear end 32 of the support strap 16 connects and extends from the rear section 28 of the headband 14. Thus, the support strap 16 extends from opposite locations on the headband 14 such that, when worn, the support strap 16 extends across and engages the top of the wearer's head. Unlike conventional headgear, the top head support strap 16 of the present invention extends in a front-to-back disposition on the head of the wearer instead of a side-to-side disposition. Accordingly, when worn, the support strap 16 extends on the top of the head of the wearer from a front center location 34 of the headband 14 on the forehead of the wearer to a rear center location 36 of the headband 14 on a rear of the head of the wearer.

According to one contemplated embodiment, the headband 14 and support strap 16 can be made of a lightweight plastic material and at least parts of each can be integrally formed and/or molded together. For example, the majority of the headband 14 can be molded as an elongate strip of material having opposite free ends 14a and 14b, and a front length 16a of the support strap 16 can be molded and formed integral with the headband 14 extending laterally from the front center location 34 of the elongate strip of material producing a "T"-shaped configuration. During assembly, the free ends 14a and 14b of the headband 14 can be secured together with a separate headband connecter 38 to form an endless loop and a separately formed end length 16b of the support strap 16 can be connected to the front length 16a of the support strap 16 with a separate support strap connector 40 and to the rear of the headband 14 to the headband connector 38. This assembly disposes the support strap 16 in a bowed or arcuate configuration where it extends above the headband 14.

The connectors 38 and 40 of the headband 14 and support strap 16 can each provide adjustment mechanisms to permit the size or circumference of the loop formed by the headband 14 and the length or radius of curvature of the support strap 16 to be manually adjusted to ensure a proper fit of the headband 14 and support strap 16 on the head of a particular wearer. For this purpose, a set of adjustment knobs, 42 and 44, can be provided as part of the connectors, 38 and 40. For example, the formed free ends 14a and 14b of the headband 14 can include slot openings, 46 and 48, each having edges formed with gear teeth or like elements 50 that overlap and become engaged and locked to the adjustment knob, 42 or 44, of the respective connector, 38 or 40. Thus, the adjustment knob 42 engages and captures the teeth 50 of both overlapping ends 14a and 14b of the headband 14 and can be used to reduce or enlarge the circumference of the endless loop of the headband 14 by rotating the knob 42 in a particular direction. The separate lengths, 16a and 16b, of the support strap 16 can also include slots, 52 and 54, with gear teeth or the like where they overlap within the support strap connector 40, and the adjustment knob 48 can be used in similar fashion to shorten or expand the length of the support strap 16.

The headband 14 of the headgear 10 can also be formed with a headlamp attachment flange 56 and integral clips 58 for securing cable 60, such as fiber optic cable extending to the headlamp 12, to the headgear 10. The attachment flange 56 is provided at the front center location 34 of the headband 14 to properly locate and mount the headlamp 12. As best shown in FIG. 2, the cable clips 58 can be provided on the side sections, 22 and 24, of the headband 14 above the ears of the wearer and on the headband connector 38 corresponding to the rear of the head of the wearer. In this way, cables 60 from the headlamp 12 can be routed around the wearer's head along the side sections, 22 and 24, of the headband 14 to the rear section 28 of the headband 14. The clips 58 in the rear of the headband 14 direct the cables 60 in a downward direction as the cables 60 extend from the headgear 10 so that the cables 60 can extend along the back of the wearer and then to an illuminator (not shown) located within or adjacent the operating room. Thus, the majority of the cable 60 that extends to the floor of the operating room is positioned behind the surgeon and should not obstruct the surgeon's vision or movements.

For purposes of providing at least some degree of comfort, the inner facing surfaces of the headband 14 and support strap 16 confronting the head of the wearer can be lined with padding 62 or the like, particularly along the front section 26 of the headband 14 and front length 16a of the support strap 16. However, the headgear 10 according to the present invention also includes a separate stabilizer or rear cranial support component 64 that further greatly enhances both the stability and comfort of the headgear 10.

As best illustrated in FIG. 6, the stabilizer 64 and is generally of an openwork material for flexibility and ventilation purposes and is generally bowl-shaped so that, when worn, the stabilizer 64 comfortably cradles a significant portion of the rear of the head of the wearer thereby greatly stabilizing the position of the headgear 10 on the head of the wearer. The stabilizer 64 prevents unwanted dislodgement and movement of the headgear 10 relative to the head of the wearer. Accordingly, the stabilizer 64 makes it unnecessary to greatly tighten or over-tighten the headband 14 and support strap 16 for purposes of ensuring headgear stability while sacrificing comfort to the wearer.

In the illustrated embodiment, the stabilizer 64 includes a centrally extending band-shaped section 66 that mates, corresponds to, and engages the inward-facing surface of the rear section 28 of the headband 14 or to the headband connector 38. Thus, this central band-like section 66 is bowed and is relative flexible to match the curvature of the endless loop of the headband 14 adjacent the rear of the headband 14. When worn, the central band-shaped section 66 of the stabilizer 64 directly engages the rear of the head of the wearer underneath the headband 14 and/or headband connector 38. However, this configuration could be altered such that the band-shaped section extends exteriorly of the headband 14.

Peripheral portions 68 of the stabilizer 64 extend from the central band-shaped section 66 of the stabilizer 64 making the stabilizer 64 of a size required to engage and cup about a significant portion of the rear of the head of the wearer. The peripheral portions 68 can be in the form of support flaps, ears, extensions, or the like. In the illustrated embodiment, the stabilizer 64 includes four outwardly-extending openwork flaps, ears, extensions or the like extending essentially from the four corners of the central band-shaped section 66 in essentially diagonal directions relative to the central band-shaped section 66. For instance, two of the flaps, 70 and 72, extend below the rear section 28 of the headband 14 on opposite sides of the rear of the wearer's head and two of the flaps, 74 and 76, extend above the rear section 28 of the headband 14 on opposite side of the rear of the wearer's head. This pattern of flaps may somewhat resemble a four-leaf clover pattern, an "X" shape, a butterfly wing pattern, or the like. Each of the illustrated flaps, 70, 72, 74 and 76, is generally flexible and includes an oval, tear drop, pear-shaped, or like shaped opening.

Figure 3:
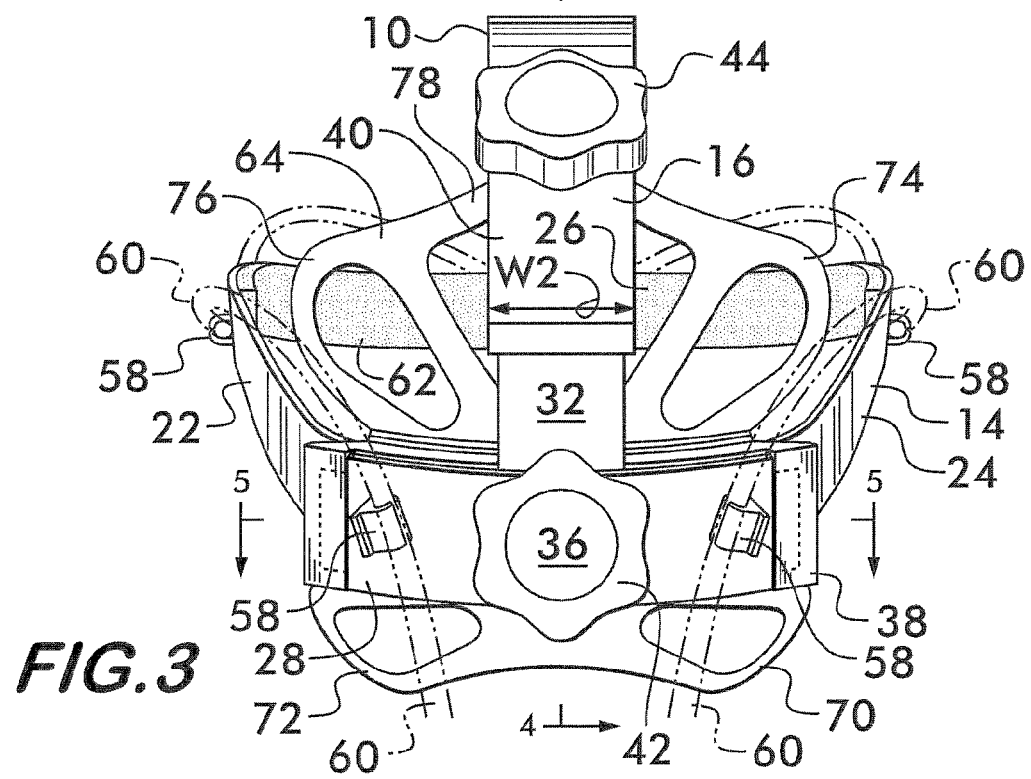
FIG. 3 is a rear elevational view of the headgear of FIG. 1.
Figure 4:
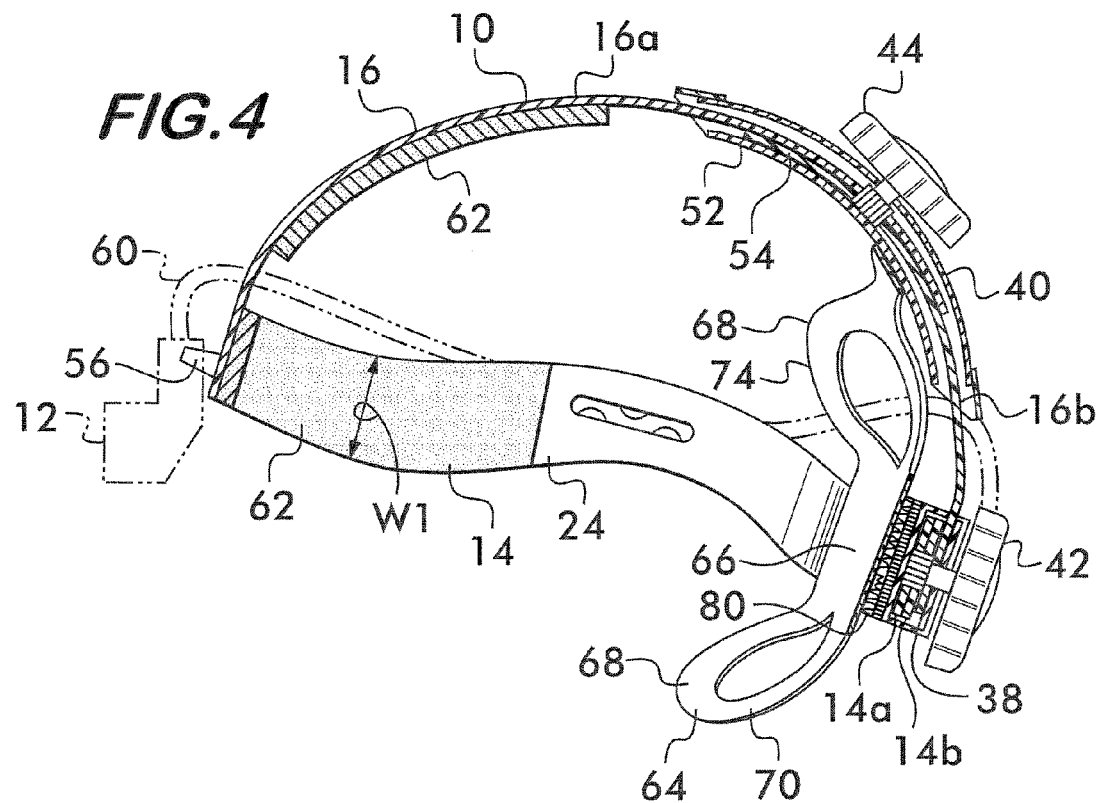
FIG. 4 is a cross-section view of the headgear of FIG. 3 along line 4-4 of FIG. 3.
Figure 5:
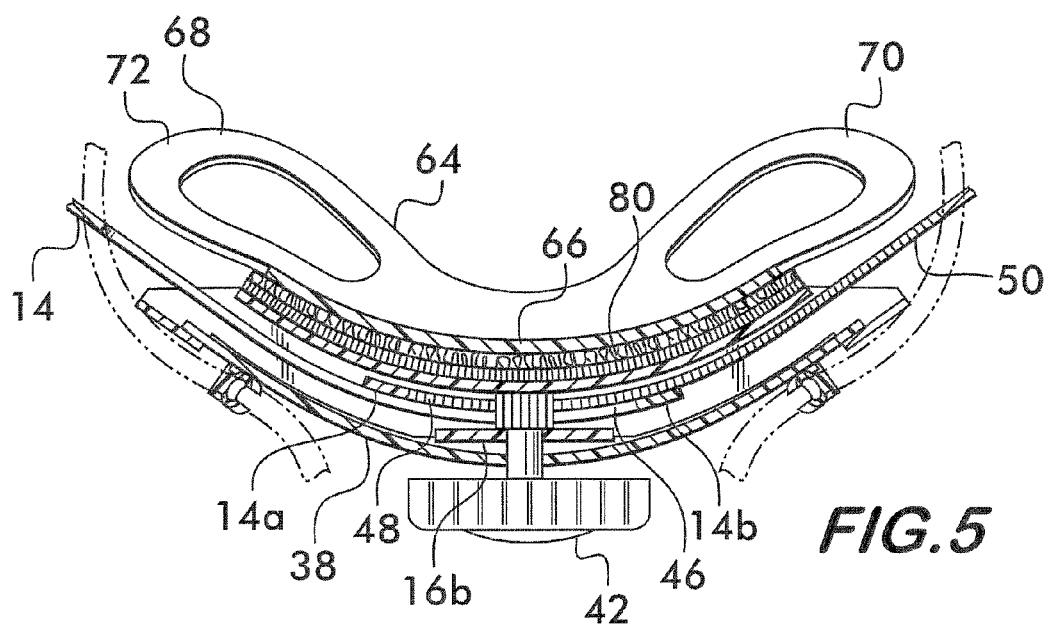
FIG. 5 is a cross-section view of the headgear of FIG. 3 along line 5-5 of FIG. 3.

In addition to the flaps, 70, 72, 74 and 76, the stabilizer 64 may also include a upper cross strip or extension 78 that interconnects the upper pair of flaps, 74 and 76, that extend above the rear section 28 of the headband 14. As best illustrated in FIGS. 1 and 3, when the headgear 10 is worn, the cross strip 78 extends underneath the support strap 16 and the two upper flaps, 74 and 76, extend on opposite sides of the support strap 16. This configuration and combination of the front-to-back disposition of the support strap 16 and use of the stabilizer 64 having peripheral portions 68 extending above and below the headband 14 and outward and laterally from both sides of the support strap 16, greatly improves stability of the headgear 10.

In FIG. 7, a showing is provided of the generally expected layout of cranial bones of a wearer. This is provided for illustrative purposes showing where the stabilizer 64 may extend on the head of a wearer. The purpose of the stabilizer 64 of the headgear 10 of the present invention is to cradle the majority, if not substantially all, of a back of the wearer's head corresponding to at least the occipital bone 82 of the cranium. The occipital bone 82 is a saucer-shaped bone located at the back and lower part of the cranium. The two lower flaps, 70 and 72, of the peripheral portion 68 of the stabilizer 64 extend along and under a lower portion of the occipital bone 82 to a location closely spaced behind about the middle of the ears of the wearer. Thus, the flaps, 70 and 72, engage and extend under the lower back of the cranium of the wearer. The upper flaps, 74 and 76, as well as the upper cross strip 78 of the stabilizer 64 extend over an upper portion of the occipital bone 82 and also extend onto a portion of the parietal bone 84 of the cranium. The upper flaps, 74 and 76, and particularly the cross strip 78, almost extend to the top of the wearer's head. Thus, the combination of the upper flaps, 74 and 76, and lower flaps, 70 and 72, cup substantially all of the back of the wearer's head corresponding to the occipital bone 82 and thereby prevent the headband 14 from any undesired movement (up, down, or skewed) relative to the wearer's head. Thus, the stability is greatly improved and eliminates any need to greatly tighten the headband 14 and support straps 16 to the head of the wearer to an extent causing discomfort. Thus, stability is not sacrificed for comfort, and comfort is not sacrificed for stability.

For purpose of example, the stabilizer 64 can be molded of a plastic, elastomeric or like material and can be made of the same or different material as the headband 14 and support strap 16. In addition, the stabilizer 64 can be removable from the headband 14 and support strap 16. Accordingly, the headgear 10 of the present invention can be worn by a surgeon with the stabilizer 64 connected to the headgear 10 as shown in FIG. 1 or with the stabilizer 64 completely removed from the headgear 10. Thus, if a particular surgeon prefers the headgear 10 without the stabilizer 64, the stabilizer 64 can be quickly removed and the headgear 10 including only the headband 14 and support strap 16 can be worn. Alternatively, if a particular surgeon prefers the added stability provided by the stabilizer 64, the stabilizer 64 can be attached to the headband 14 and worn as part of the headgear 10 as shown in FIG. 1.

For purposes of connecting/removing the stabilizer 64 relative to the headgear 10, the headgear 10 can include a stabilizer connector element 80. For example, the connector 80 can be in the form of cooperating strips of hook-and-loop fastening material that can be provided on the confronting surfaces of the stabilizer 64 and the headband 14 or headband connector 38. Of course, other attachment means can be utilized including snaps, buttons, friction-fitting components, male/female interconnections, adhesives, mechanical fasteners, clips, attachment bands, hooks, and the like.

While a preferred headgear for mounting a surgical headlight system has been described in detail, various modifications, alternations, and changes may be made without departing from the spirit and scope of the headgear according to the present invention as defined in the appended claims.

The invention claimed is:

1. Headgear for mounting a headlight, comprising:
a headband for encircling a wearer's head and for permitting the majority of a top of the wearer's head to be uncovered and exposed to ambient conditions; and
a stabilizer connectable to a rear section of the headband for engaging and cradling a substantial portion of a back of a wearer's head when the headgear is worn by a wearer, said stabilizer including a peripheral extending portion extending beneath said headband on opposite sides of the wearer's head corresponding to a location of a lower portion of a occipital bone of the wearer's head and a peripheral portion extending above said headband on opposite sides of the wearer's head corresponding to a location of a top of the occipital bone.

2. Headgear according to claim 1, further comprising a connection element for removably connecting said stabilizer to said headband such that said headband can be worn without said stabilizer when said stabilizer is removed from said headband and such that said headband can be worn with said stabilizer when said stabilizer is connected to said headband.

3. Headgear according to claim 2, wherein said connection element includes a strip of hook-and-loop fasteners for attaching said stabilizer to said headband.

4. Headgear according to claim 1, wherein said peripheral extending portion of said stabilizer that extends beneath said headband includes opposed flaps that extend below the lower portion of the wearer's occipital bone and wherein said peripheral extending portion of said stabilizer that extends above said headband includes opposed flaps that extend over an upper portion of the occipital bone and onto a parietal bone of the wearer's head thereby enabling said stabilizer to cup a portion of the back of the wearer's head of a size substantially corresponding to a size of the wearer's occipital bone.

5. Headgear according to claim 1, wherein said stabilizer is a thin openwork member having numerous openings, and wherein said stabilizer is bowed to match a contour of a lower back of the wearer's head.

6. Headgear according to claim 1, wherein said peripheral extending portion of said stabilizer that extends beneath said headband includes a pair of lower flaps and wherein said peripheral extending portion of said stabilizer that extends above said headband includes a pair of upper flaps, and wherein said stabilizer includes a cross strip interconnecting upper sections of said upper flaps at a location above said headband.

7. Headgear according to claim 6, further comprising a support strap extending from a rear of the headband to a front of the headband such that, when the headgear is worn, the support strap extends on the top of the wearer's head from a back of the head to the front of the head, and wherein said upper flaps of said stabilizer extend on opposite sides of said support strap and said cross strip of said stabilizer extends underneath said support strap.

8. Headgear according to claim 1, wherein said headband includes a headlamp mounting flange and cable guide clips.

9. Headgear for mounting a fiber optic surgical headlight, comprising:
an elongate endless headband for encircling the head of a wearer, said headband including a front section for extending laterally across a forehead of the wearer, a rear section for extending laterally across a back of the wearer's head, and side sections extending across a side of the wearer's head above the wearer's ears;
an elongate support strap having one end connected to said front section of said headband and an opposite end connected to a rear section of said headband, said headband and support strap having relatively narrow widths permitting a majority of a top of the wearer's head to remain uncovered by the headgear and exposed to ambient conditions; and
a stabilizer connectable to the rear section of the headband for engaging and cradling at least a lower back region of the wearer's head when the headgear is worn by a wearer, said stabilizer including peripheral portions extending below said headband on opposite sides of the wearer's head and peripheral portions extending above said headband on opposite sides of the wearer's head and opposite sides of said support strap.

10. Headgear according to claim 9, further comprising a connection element for removably connecting said stabilizer to said headband such that said headband can be worn without said stabilizer when said stabilizer is removed from said headband and such that said headband can be worn with said stabilizer when said stabilizer is connected to said headband.

11. Headgear according to claim 10, wherein said connection element includes a strip of hook-and-loop fasteners for attaching said stabilizer to said headband.

12. Headgear according to claim 10, wherein said peripheral portions of said stabilizer that extend below said headband include opposed flaps that extend below the lower portion of the wearer's occipital bone and wherein said peripheral portions of said stabilizer that extend above said headband includes opposed flaps that extend over an upper portion of the occipital bone and onto a parietal bone of the wearer's head thereby enabling said stabilizer to cup a portion of the back of the wearer's head of a size substantially corresponding to a size of the wearer's occipital bone.

13. Headgear according to claim 12, wherein said stabilizer is openwork with each of said flaps having an opening, and wherein said stabilizer is bowed to match a contour of the lower back region of the wearer's head.

14. Headgear according to claim 13, wherein said stabilizer includes a cross strip interconnecting upper sections of said opposed flaps extending above said headband, and wherein said cross strip of said stabilizer extends above said headband and underneath said support strap.

15. Headgear according to claim 14, wherein said front section of said headband includes a headlamp mounting flange and at least said side sections of said headband include cable guide clips.

16. A fiber optic surgical headlight system, comprising:
headgear for being worn on a head of a surgeon; and
a headlamp mounted on said headgear;
said headgear including an elongate headband for encircling the head of a wearer, said headband including a front section for extending laterally across a forehead of the wearer and on which said headlamp is mounted, a rear section for extending laterally across a rear of the wearer's head, and side sections extending across a side of the wearer's head above the wearer's ears;
said headgear including an elongate support strap having one end connected to said front section of said headband adjacent said headlamp and an opposite end connected to a rear section of said headband, said headband and support strap having relatively narrow widths permitting a majority of the wearer's head to remain uncovered by the headgear and exposed to ambient conditions; and
said headgear including a stabilizer removably connectable to the rear of the headband for engaging and cradling a lower back region of the wearer's head when the headgear is worn by a wearer, said stabilizer including peripheral portions extending laterally and downwardly below said rear section of said headband on opposite sides of the rear of the wearer's head and peripheral portions extending laterally and upwardly above said rear section of said headband on opposite sides of the rear of the wearer's head and on opposite sides of said support strap.

17. A fiber optic surgical headlight system according to claim 16, further comprising a strip of hook-and-loop fasteners between said stabilizer and said headband for removably attaching said stabilizer to said headband.

18. A fiber optic surgical headlight system according to claim 16, wherein, when worn, said peripheral portions extending below said headband extend over a lower portion of the wearer's head corresponding to a location of a lower portion of an occipital bone of the wearer to a location slightly spaced behind a mid-height of the wearer's ears and said peripheral portions extending above said headband extend over a portion of the wearer's head corresponding to an upper portion of the occipital bone and onto a portion of a parietal bone of the wearer.

19. A fiber optic surgical headlight system according to claim 18, wherein said stabilizer is openwork with each of said peripheral portions having an opening, wherein said stabilizer is bowed to match a contour of a rear of a wearer's head, wherein said stabilizer includes a cross strip interconnecting upper sections said peripheral portions extending above said headband, and wherein said cross strip of said stabilizer extends above said headband and underneath said support strap.

\* \* \* \* \*